United States Patent [19]

Cross

[11] Patent Number: 5,015,244
[45] Date of Patent: May 14, 1991

[54] ADHESIVE RING ASSEMBLIES FOR COLLECTION BAGS

[75] Inventor: David E. Cross, Rustington, England

[73] Assignee: Smiths Industries Public Limited Company, London, England

[21] Appl. No.: 426,608

[22] Filed: Oct. 25, 1989

[30] Foreign Application Priority Data

Nov. 8, 1988 [GB] United Kingdom ............... 8826151
Jan. 10, 1989 [GB] United Kingdom ............... 8900494

[51] Int. Cl.$^5$ .............................................. A61F 5/44
[52] U.S. Cl. ................................. 604/344; 604/344; 604/338
[58] Field of Search ............... 604/344, 343; 264/135; D24/49, 34, 51, 58; 128/82, 155

[56] References Cited

U.S. PATENT DOCUMENTS

| | | | |
|---|---|---|---|
| 1,949,271 | 2/1934 | Duhamel | D24/49 |
| 2,233,209 | 2/1941 | Herzog | D24/49 X |
| 3,897,780 | 8/1975 | Trousil | 604/344 |

FOREIGN PATENT DOCUMENTS 2035096 6/1980 United Kingdom .
2128479 5/1984 United Kingdom .

Primary Examiner—Randall L. Green
Assistant Examiner—Gina B. Gualtieri
Attorney, Agent, or Firm—Pollock, Vande Sande and Priddy

[57] ABSTRACT

An adhesive ring assembly for an ostomy bag comprises a circular ring of adhesive around the opening of the bag and protected by two release paper sheets. The release sheets are of siliconized paper and are of an annular shape. Each sheet is folded in half along its diameter so that one half releasably adheres to the adhesive and the second half overlays the first half. The folded edge of one sheet overlaps the folded edge of the other sheet. The release sheets are removed by pulling the edge of each second half parallel to the ring so that each sheet peels away from the adhesive from its folded edge.

6 Claims, 3 Drawing Sheets

ADHESIVE RING ASSEMBLIES FOR COLLECTION BAGS

BACKGROUND OF THE INVENTION

This invention relates to adhesive ring assemblies for collection bags.

The invention is more particularly concerned with rings for use with ostomy bags or the like which are secured around a body opening to collect waste material discharged therefrom.

Conventional adhesive rings are made from a karaya substance, a rubber-based adhesive, an acrylic-based adhesive, or a hydrophilic polymer in a support matrix of a hydrophobic polymer, such as SEEL-A-PEEL (a Registered Trade Mark of Eschmann Bros. & Walsh Limited). The ring may be pre-assembled on the bag, around its body waste opening and have a release sheet, such as of siliconized paper on its outer surface to protect it in packaging and during handling. The release sheet is of the same size and shape as the adhesive ring, with a tab projecting from one side to facilitate gripping the sheet and peeling it from the ring.

In use, the user peels the release sheet entirely away from the adhesive ring, then positions the ring around the stoma or other body waste opening and smooths the ring against the skin to form a secure mechanical coupling and a fluid-tight seal of the bag with the body discharge opening.

Several problems can arise with this arrangement. If the ring is not correctly positioned initially and it has to be removed from the skin and repositioned, this can cause the ring to become wrinkled leading to a reduction in the effectiveness of the seal provided by the ring. Also, if the ring should be incorrectly positioned so that it comes into contact with the body opening, this can cause contamination of the adhesive surface by mucus, faeces or the like which also reduces the effectiveness of the ring and can make it necessary to replace the entire bag.

It is of great importance that users of such collection bags should have confidence that the ring will provide secure retention of the bag in position and will not allow leakage between the ring and the skin.

The adhesive rings are not confined to use where they directly contact the skin but they can be used in conjuction with a peristomal wafer secured to the skin or to retain a collection bag on a separate coupling which is secured to the skin and which is used repeatedly as bags are replaced.

BRIEF SUMMARY OF THE INVENTION

It is an object of the present invention to provide an adhesive ring assembly that can be used to alleviate the above-mentioned problems.

According to one aspect of the present invention there is provided an adhesive ring assembly for collection bag comprising a ring for use in securing the collection bag to a region around a body waste opening, the ring having an adhesive surface and at least one release sheet, the release sheet being folded back on itself with a first part of the release sheet releaseably adhered to the ring and a second part overlaying the first part so that the release sheet can be removed from the ring by pulling the second part substantially parallel to the ring so that it peels away from the ring from the region where the sheet is folded.

The assembly preferably includes two release sheets, each sheet having a first part releasably adhered to a respective different part of the ring and a second part folded back to overlay the first part, and the folded edge of the two sheets lying adjacent one another so that each sheet can be peeled away from the adhesive surface by pulling from opposite edges of the assembly. The folded edge of one sheet preferably overlaps the folded edge of the other sheet. The two sheets may have a central aperture of circular shape and may be folded substantially in half. The or each release sheet is preferably of a siliconized paper. The collection bag may be an ostomy bag and the body waste opening a stoma.

According to another aspect of the present invention there is provided an ostomy bag including an adhesive ring assembly according to the above one aspect of the invention.

A two-part w.c. disposable ostomy bag assembly with an adhesive ring assembly, in accordance with the present invention, will now be described, by way of example, with reference to the accompanying drawings.

DETAILED DESCRIPTION OF THE PREFERRED EMBODIMENT

Figure 1:
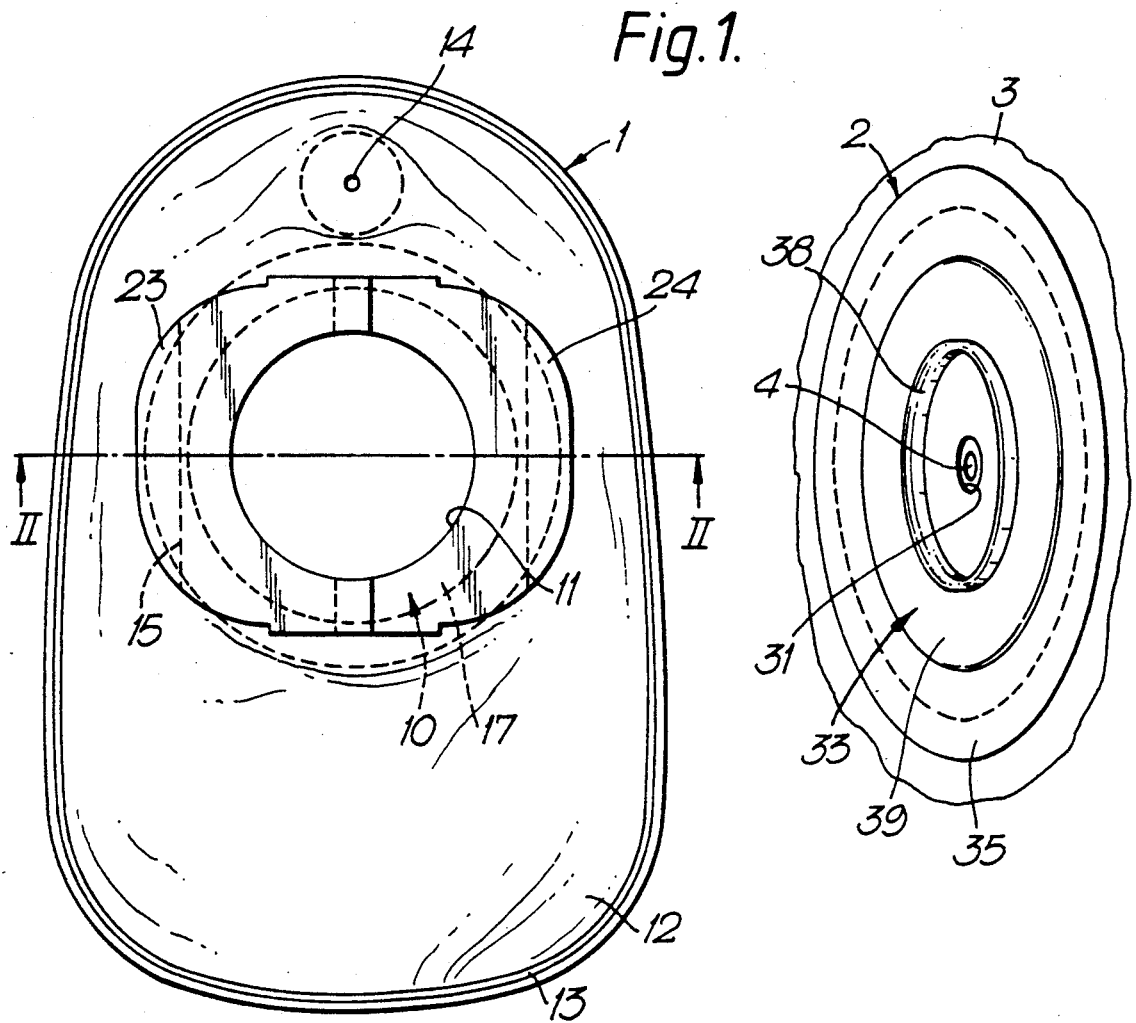
FIG. 1 is a front view of the bag assembly separated.

With reference to FIG. 1, the assembly comprises a w.c. disposable ostomy bag 1 and a user fitment 2 that is secured to the skin 3 of the user around a stoma 4. The bag 1 is provided with a coupling 10 around its opening 11 that can be secured to the fitment 2 and removed from it when necessary, leaving the fitment in position on the user.

Figure 2:
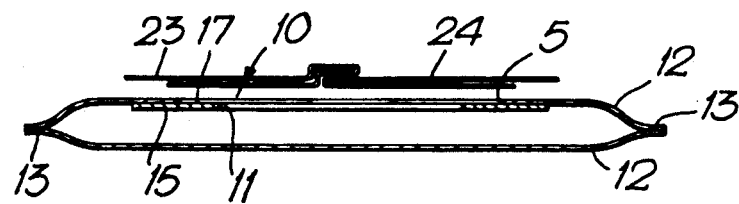
FIG. 2 is a sectional view along the line II—II of FIG. 1.
Figure 3:
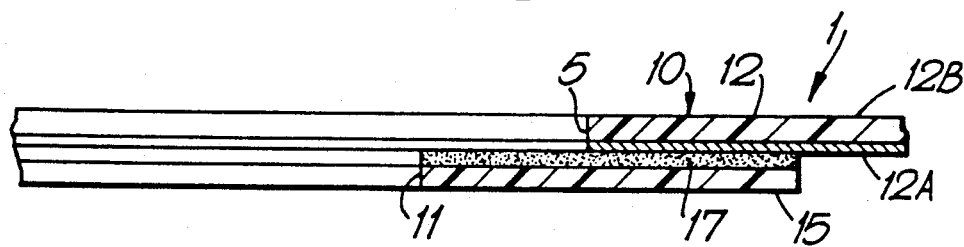
FIG. 3 is a sectional view of a part of the bag to a larger scale.

With reference now also to FIGS. 2 and 3, the bag 1 has two flexible plastics sheets 12 of a w.c. disposable material which are welded together around their edge 13 to form the walls of a bag that is sealed apart from its opening 11 and an optional filtered flatus vent 14. The material used to form the sheets 12 may be of the kind used in the ostomy bag sold by Eschmann Bros. & Walsh Limited under the trade mark SYMPHONY. The material comprises a thin, water resistant layer 12A that is presented inwardly to the contents of the bag and a thicker outer layer 12B that is broken up or dispersed in turbulent cold water so that the inner layer can collapse or break up without providing an obstacle to flushing. A circular aperture 5 is formed in the sheet 12 which, in use, is against the body of the user. The coupling 10 is shown in more detail in FIG. 3 and includes an annular stiffening ring or flange 15 secured to the inner surface of the sheet 12 around the aperture 5 by means of a ring 17 of adhesive material on the front surface on the flange. The flange 15 is of a bendable plastics material which is stiffer than the sheet 12 and is of circular shape. The outside diameter of the flange 15 is larger than the diameter of the aperture 5 in the sheet 12, whereas the inside diameter of the flange 15 is smaller than the aperture, so that the central opening of the flange provides the opening 11 to the bag. About half the width of the flange 15 is exposed within the aperture 5 so that the inner part of the adhesive ring 17 is also exposed around the opening 11 of the bag. Prior to use, the exposed part of the front surface of the adhesive ring 17 is protected by two release sheets 23 and 24.

Each release sheet 23 and 24 is of a non-adhesive material, such as siliconized paper, which can be removed readily from the exposed part of the adhesive ring 17. The sheets 23 and 24 are both of annular shape with a circular central aperture the same diameter as the opening 11 and are generally square in shape externally with rounded corners. The sheets 23 and 24 are folded along a line close to their diameter so that one half of the sheet overlies the other; the underneath half of each sheet releasably adheres to the adhesive ring 17 while the other half is free, as shown in FIG. 2. The release sheets 23 and 24 are, in fact, slightly larger, when opened flat, than the exposed part of the adhesive ring 17 so that their folded edges overlap one another on the adhesive, thereby ensuring that none of the adhesive is exposed.

Figure 4:
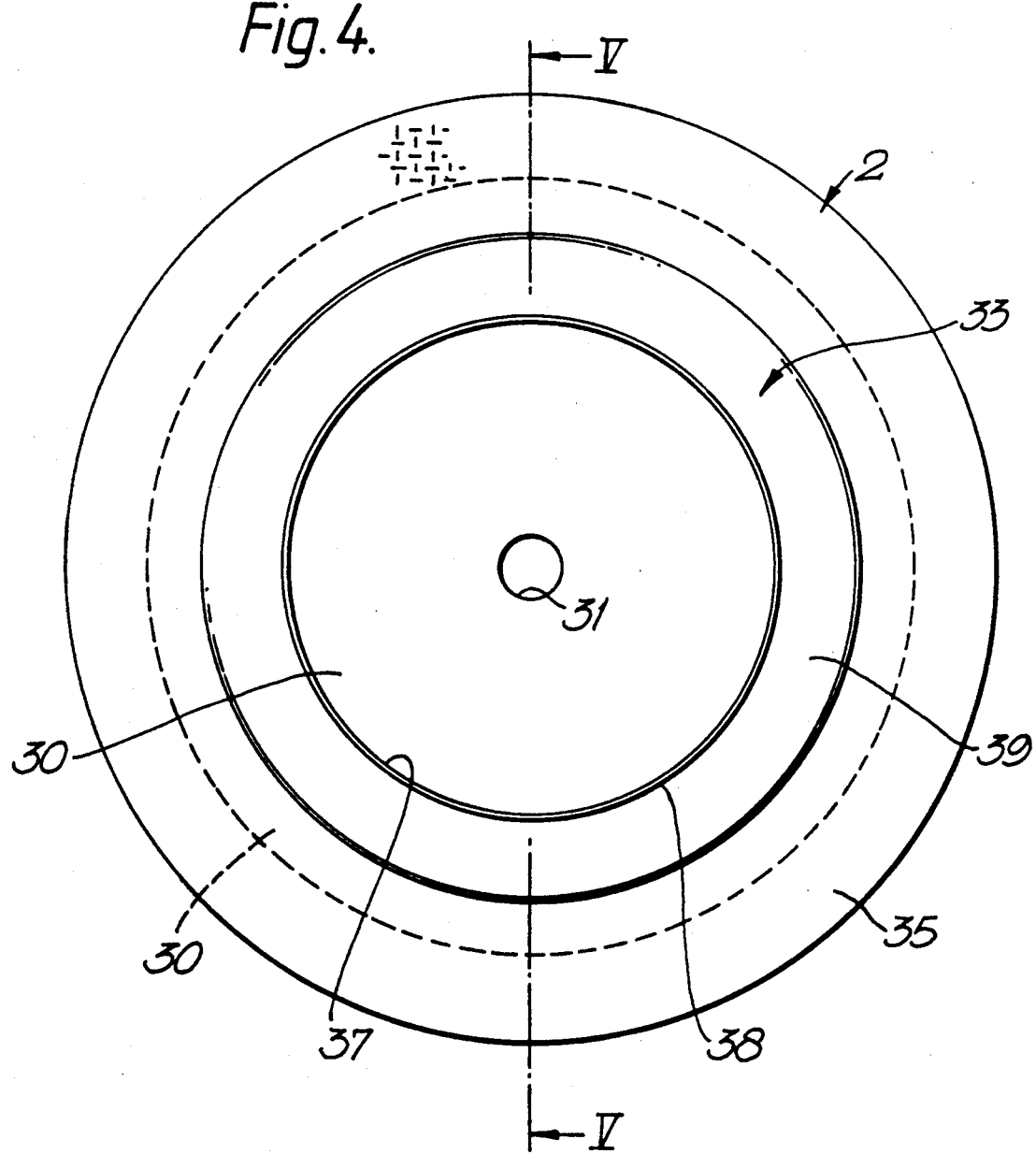
FIG. 4 is a front view of the patient fitment.
Figure 5:
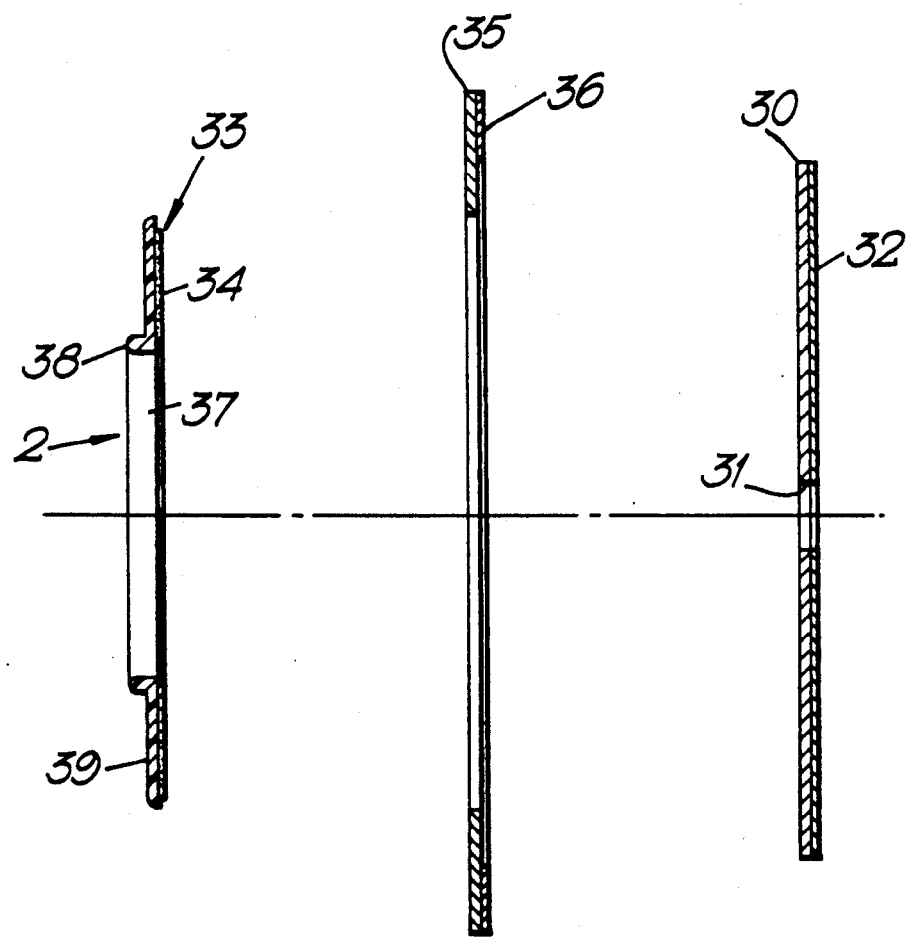
FIG. 5 is a exploded sectional view along the line V—V of FIG. 4.

With reference now also to FIGS. 4 and 5, the user fitment 2 is secured to the user's skin 3 by means of an adhesive layer in the form of a disc 30 on the rear of the fitment. The disc 30 is of a hydrophilic polymer in a support matrix of a hydrophobic polymer, such as SEEL-A-PEEL (a Registered Trade Mark of Eschmann Bros. & Walsh Limited). The disc 30 is circular with a central aperture 31, selected in size according to the size of the user's stoma 4. Prior to use, the rear surface of the disc 30 is protected by a release sheet 32.

An annular, circular plate member 33, moulded from a semi-rigid but bendable plastics, is adhered to the front surface of the disc 30 by means of an adhesive 34 on the rear surface of the plate. The outer diameter of the plate 33 is less than that of the disc 30, the exposed periphery of the disc being covered by an annular ring 35 of microporous tape which is thinner than the disc. The external diameter of the microporous ring 35 is greater than that of the disc 30 so that it overlaps the disc around its outer edge. The rear surface of the ring 35 is adhesive and is protected, prior to use, where it overlaps the disc 30, by an annular release sheet 36.

The plate 33 is about 0.5 mm thick with a central aperture 37 around which a locating collar 38 projects forwardly. The height of the collar 38 above the plate 33 is about 3 mm, which is at least high enough to project through the coupling 10. Its external diameter is slightly smaller than the diameter of the aperture 11 in the flange 15 of the bag coupling 10. Around the outside of the collar 38, the plate 33 provides a flat, planar, front surface 39 which is non-adhesive but which can form a secure, releasable sealing bond with the adhesive layer 17 on the bag coupling 10.

In use, the user first secures the fitment 2 to the skin 3 around the stoma 4 by removing the release sheet 32 from the disc 30 and the release sheet 36 from the microporous ring 35 and smoothing the disc and sheet onto the skin. The microporous ring 35 helps prevent the outer edge of the disc 30 lifting away from the skin.

The user then takes hold of the ostomy bag 1, with its release sheets 23 and 24 still in position, and places it against the fitment 2 so that the collar 38 locates in the opening 11 of the bag, and so that the bag is correctly aligned to hang vertically. The free edge of each release sheet 23 and 24 is then gripped in turn and pulled outwardly, parallel to the surface of the bag 1 so that they peel away from the center the adhesive ring 17. In this way, the underlying adhesive 17 is exposed and can be brought into contact with the front surface 39 of the plate 33 by gentle pressure. This provides secure retention of the bag 1 on the fitment 2 and seals the coupling between the bag and the fitment against leakage of body waste products entering the bag.

When the bag 1 needs to be removed, the user grips both the bag 1 and the plate 33 and peels the bag coupling 10 away from the patient fitment 2, leaving the fitment in position on the user's skin. The bag 1 is then squeezed to expel air and gas through the opening 11 and the bag folded about a diameter of the flexible flange 15 so that the surface of the adhesive layer 17 is folded on top of itself and seals the opening. Alternatively, the bag 1 can be sealed in this way prior to expelling gas through the flatus vent 14 by squeezing. This effectively prevents air entering the bag so that it can be dropped into the pan of a w.c. with less risk of floating. The fitment 2 need only be replaced after several days.

The thin, flexible nature of the flange 15 and hence the coupling 10 ensures that it can be flushed away around the waste pipe of a w.c. without obstruction. The adhesive 17 can also be water soluble which facilitates disposal of the bag.

With a bag assembly of this kind it is possible to provide a secure coupling with a low profile so that there is no conspicuous bulge beneath the user's clothing. The user part of the coupling can also be made bendable so that it conforms with the anatomy.

Various modifications to the assembly are possible. For example, the flange 15 could be joined to the outer surface of the bag. It is preferable for the release sheets 2S and 24 to be removable when the bag 1 is adjacent the patient fitment such as by pulling a part of the sheets overlaying an outer region of the adhesive, but this can be achieved with different arrangements of release sheets.

The invention is not confined to use with w.c. disposable bags or with two-part bags but could be used with any oonventional medico-surgical collection bag.

What I claim is:

1. An adhesive ring assembly for a collection bag comprising: a ring; means for securing said ring to said collection bag; an adhesive surface on said ring by which the collection bag is secured to a region around a body waste opening; and two release sheets, each release sheet having a central aperture and being folded substantially in half back on itself across its length to form a first part, an associated second part and a folded edge therebetween, the first parts being releasably adhered to respective different parts of the ring and the second parts being at least as long as the associated first parts so that they overlie the associated first parts and extend to opposite edges of the ring assembly, the said folded edges of the two release sheets lying adjacent one another so that each said sheet can be peeled away from the adhesive surface by pulling the second parts of the sheets from opposite edges of the ring assembly in directions substantially parallel to the ring while the ring assembly is held up to said region around the body waste opening to peel the release sheets away from the ring from the region where the sheets are folded.

2. An adhesive ring assembly according to claim 1, wherein the folded edge of one sheet overlaps the folded edge of the other sheet.

3. An adhesive ring assembly according to claim 1, wherein each release sheet is of a siliconized paper.

4. An ostomy bag assembly comprising an ostomy bag, said ostomy bag having an opening thereto by which body waste material can enter the bag from a stoma, and an adhesive ring assembly comprising: a ring; means securing said ring around said opening to the ostomy bag; an adhesive surface on said ring by which the ostomy bag can be secured to a region around the stoma; and two release sheets, each release sheet having a central aperture and being folded substantially in half back on itself across its length to form a first part, an associated second part and a folded edge, each said first part being releasably adhered to a respective different part of the ring, and each said second part being at least as long as the associated first part so that it overlies said associated first part and extends to an edge of the ring assembly, the said folded edges lying adjacent one another so that the release sheets can be removed from the adhesive surface of the ring by gripping the second parts toward the edge of the ring assembly and pulling them from opposite edges of the assembly in directions substantially parallel to the ring while the ring assembly is held up to the stoma so that each release sheet peels away from the ring from its said folded edge.

5. An ostomy bag assembly according to claim 4, wherein the folded edge of one sheet overlaps the folded edge of the other sheet.

6. An ostomy bag assembly according to claim 4, wherein each release sheet is of a siliconized paper.

* * * * *